United States Patent

Altermatt

[11] 4,051,120
[45] Sept. 27, 1977

[54] MONOAZO COMPOUNDS HAVING A 5-NITROTHIAZOLYL-2 DIAZO COMPONENT RADICAL AND A 1,4-PHENYLENE COUPLING COMPONENT RADICAL HAVING AN N-(ALKYL OR ALLYL)-N-(ALKOXYL- OR ALKOXYETHOXY-ETHOXYCARBONYLOX-YALKYL)AMINO GROUP IN ITS PARA POSITION

[75] Inventor: Ruedi Altermatt, Buckten, Switzerland

[73] Assignee: Sandoz Ltd., Basel, Switzerland

[21] Appl. No.: 613,216

[22] Filed: Sept. 15, 1975

[30] Foreign Application Priority Data

Sept. 19, 1974 Switzerland .................. 12726/74

[51] Int. Cl.$^2$ .................. C09B 29/08; C09B 29/26; D06P 1/18; D06P 2/42
[52] U.S. Cl. .................. 260/158; 260/306.8 R; 260/463; 260/573
[58] Field of Search .................. 360/158

[56] References Cited

U.S. PATENT DOCUMENTS

| | | | |
|---|---|---|---|
| 3,097,198 | 7/1963 | Fishwick et al. | 260/207.1 |
| 3,553,190 | 1/1971 | Anderton et al. | 260/207 |
| 3,586,663 | 6/1971 | Kruckenberg | 260/207.1 |
| 3,592,807 | 7/1971 | Von Brachel et al. | 260/207.1 |
| 3,709,872 | 1/1973 | Koller | 260/207.1 |

FOREIGN PATENT DOCUMENTS

| | | | |
|---|---|---|---|
| 1,390,146 | 1/1965 | France | 260/158 |
| 2,351,951 | 4/1974 | Germany | 260/158 |
| 1,263,416 | 2/1972 | United Kingdom | 260/158 |
| 1,273,228 | 3/1972 | United Kingdom | 260/158 |
| 1,281,778 | 7/1972 | United Kingdom | 260/158 |

*Primary Examiner*—Floyd D. Higel
*Attorney, Agent, or Firm*—Gerald D. Sharkin; Richard E. Vila; Melvyn M. Kassenoff

[57] ABSTRACT

Disclosed are compounds of the formula,

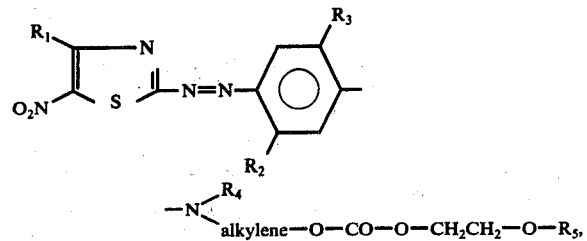

wherein
$R_1$ signifies hydrogen, alkyl, unsubstituted phenyl or phenyl substituted by up to three substituents selected from chlorine, bromine and cyano, provided a maximum of one cyano is borne thereby,
$R_2$ signifies alkyl or alkoxy,
$R_3$ signifies hydrogen, alkyl or alkoxy,
$R_4$ signifies alkyl or allyl,
$R_5$ signifies alkyl or $\beta$-alkoxyethyl, and alkylene is of 2 to 4 carbon atoms, there being at least 2 carbon atoms in the chain, their production and use as disperse dyes, particularly for linear aromatic polyester, cellulose 2½ acetate, cellulose triacetate and synthetic polyamide substrates. The obtained dyeings possess satisfactory fastness to light, thermofixation, sublimation, pleating, water, washing, perspiration, solvents, lubricants, rubbing, cross-dyeing, ozone, gas fumes and chlorine and resistance to various permanent-press processes, soil release finishing and reduction.

9 Claims, No Drawings

MONOAZO COMPOUNDS HAVING A 5-NITROTHIAZOLYL-2 DIAZO COMPONENT RADICAL AND A 1,4-PHENYLENE COUPLING COMPONENT RADICAL HAVING AN N-(ALKYL OR ALLYL)-N-(ALKOXYL- OR ALKOXYETHOXY-ETHOXYCARBONYLOXYALKYL)AMINO GROUP IN ITS PARA POSITION

The invention relates to monoazo compounds.
The invention provides compounds of formula I

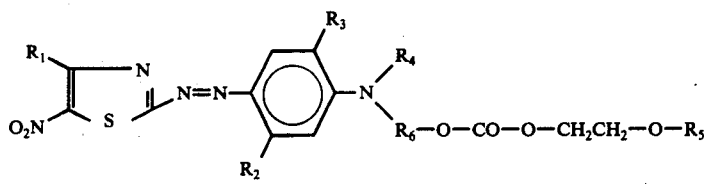

wherein
- $R_1$ signifies hydrogen, alkyl, unsubstituted phenyl or phenyl substituted by up to three substituents selected from chlorine, bromine and cyano, provided a maximum of one cyano is borne thereby,
- $R_2$ signifies alkyl or alkoxy,
- $R_3$ signifies hydrogen, alkyl or alkoxy,
- $R_4$ signifies alkyl or allyl,
- $R_5$ signifies alkyl or β-alkoxyethyl, and
- $R_6$ is alkylene of 2 top 4 carbon atoms, there being at least 2 carbon atoms in the chain.

Any alkyl radical or moiety in the compounds of formula I preferably contains 1 to 4, more preferably 1 or 2, carbon atoms, except in the case, of any alkyl as $R_4$ which is more preferably of 2 or 3 carbon atoms.

When $R_1$ signifies substituted phenyl, such is preferably monosubstituted. In the compounds of formula I, $R_1$ is preferably methyl or hydrogen, more preferably hydrogen. $R_2$ is preferably methoxy or methyl, more preferably methyl. $R_3$ is preferably hydrogen. $R_4$ is preferably ethyl, propyl or allyl, more preferably ethyl. $R_5$ is preferably methyl, ethyl, β-methoxyethyl or β-ethoxyethyl, more preferably methyl or ethyl, most preferably ethyl. $R_6$ is preferably ethylene.

In a preferred class of compounds of the invention, $R_1$ is hydrogen or methyl, $R_2$ is methyl or methoxy, $R_3$ is hydrogen, $R_4$ is ethyl, $R_5$ is methyl, ethyl, β-methoxyethyl or β-ethoxyethyl and $R_6$ is as defined in connection with formula I, preferably ethylene.

In a more preferred class of compounds $R_1$ is hydrogen or methyl, $R_2$ is methyl, $R_3$ is hydrogen, $R_4$ is ethyl, $R_5$ is methyl or ethyl, and $R_6$ is ethylene, the most preferred compound being of such class but where $R_1$ is hydrogen and $R_5$ is ethyl.

The invention also provides a process for the production of the compounds of formula I
comprising coupling a diazonium salt of an amine of formula II

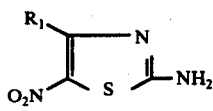

where $R_1$ is as defined above, with a compound of formula III,

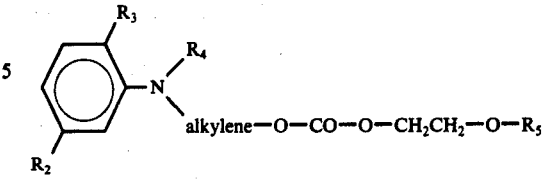

in which $R_2$ to $R_5$ and alkylene are as defined above.

The process may be carried out in conventional manner, e.g. in an acid, optionally buffered, medium, e.g. in the pH-region of below 5. Temperatures of below 20° C, preferably between −5° and +5° C, are suitably employed. The buffering agents are preferably alkali metal salts of lower alkanoic acids, e.g. of acetic acid or propionic acid, sodium acetate being the preferred buffering agent.

The resulting compounds may be isolated and purified in conventional manner.

The compounds of formula II are known or may be obtained in conventional manner from available starting materials.

The compounds of formula III may be produced by condensation, in equimolar proportions, of a glycol ether of the formula $R_5$—O—$CH_2CH_2$—OH with phosgene, and by condensation of the reaction product thereby formed with equimolar proportion of a compound of formula IV,

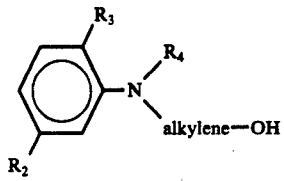

where $R_2$ to $R_4$ and alkylene are as defined above.

Such process is conveniently carried out in conventional manner for the type of reaction involved, e.g. in a water-free, inert solvent, e.g. pyridine.

The compounds of formula I are disperse dyes and are indicated for use in the dyeing or printing of substrates, particularly textile substrates, of fully or semi-synthetic hydrophobic, high molecular weight organic material, particularly of linear aromatic polyester, cellulose-2½-acetate cellulose triacetate and synthetic polyamide material. The dyeing or printing of such substrates may be carried out in conventional manner, e.g. as described in French Pat. No. 1,445,371, employing conventional amounts of the dyestuffs.

The compounds of formula I are preferably employed in the form of dyeing preparations, prepared in conventional manner, such as by grinding with dispersing agents or fillers and drying using vacuum or spray drying techniques.

The compounds of formula I have good affinity for the substrates dyeable therewith, of particular interest being the good affinity thereof for cellulose acetate substrates. Further, the dyeings obtained have satisfactory all-round fastness properties, e.g. to light, thermofixation, sublimation, pleating, water, sea water, washing, perspiration, to solvents, such as dry cleaning solvents and lubricants, to rubbing, cross-dyeing, ozone, gas fumes and chlorine. They show resistance to the various permanent-press processes and to soil-release finishing. The dischargeability of the dyes and resistance to reduction, as well as their reserving effect on wool and cotton, are also good.

The following Examples, in which all parts and percentages are by weight, and all temperatures in degrees centigrade, illustrate the invention.

EXAMPLE 1

14.5 Parts of 2-amino-5-nitrothiazole are added slowly, at 0°–5°, to a mixture consisting of 107 parts of nitrosyl-sulphuric acid (produced by dissolving 7 parts of sodium nitrite in 100 parts of concentrated sulphuric acid), 85 parts of glacial acetic acid and 15 parts of propionic acid. A mixture of 85 parts of glacial acetic acid and 15 parts of propionic acid are added to the mixture obtained at 0°–5°, and they are subsequently stirred for 3 hours at 0°–5°.

A solution of 29.5 parts of the compound of the formula

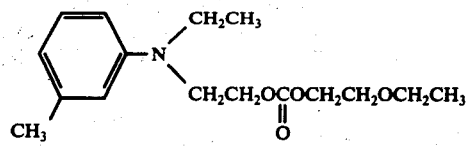

in 85 parts of glacial acetic acid and 15 parts of propionic acid is added slowly with stirring, and the resultant coupling mixture is stirred for 3 hours at 0°–5°. The reaction mixture is poured, with stirring, into a mixture consisting of 600 parts of ice and 300 parts of water, and the dyestuff is precipitated. It is filtered off, washed until acid and salt-free with water and dried. The dyestuff obtained dyes synthetic fibres in blue shades with notable all-round fastness properties. It is of the formula

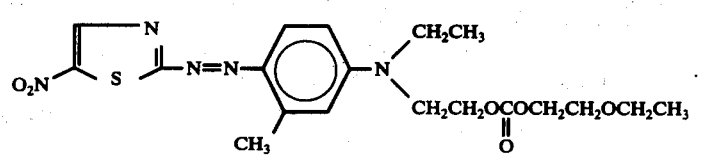

In the following table are given further compounds of formula I which may be produced in a manner similar to that of Example 1, employing appropriate starting materials. On polyester material they all give dyeings of a blue shade with notable all-round fastness properties.

TABLE

| Ex. No. | $R_1$ | $R_2$ | $R_3$ | $R_4$ | $R_6$ | $R_5$ |
|---|---|---|---|---|---|---|
| 2 | —$CH_3$ | —$CH_3$ | H | —$C_2H_5$ | —$CH_2CH_2$— | —$C_2H_5$ |
| 3 | H | —$OCH_3$ | H | " | " | " |
| 4 | H | —$CH_3$ | H | " | " | —$CH_3$ |
| 5 | H | " | H | " | " | —$CH_2CH_2OCH_3$ |
| 6 | —$C_6H_5$ | " | H | " | " | —$C_2H_5$ |
| 7 | —C$_6$H$_4$—Br | " | H | " | " | " |
| 8 | —C$_6$H$_4$—Cl | " | H | " | " | " |
| 9 | —C$_6$H$_4$—CN | " | H | " | " | " |
| 10 | H | —$OC_2H_5$ | H | " | " | " |
| 11 | —$C_2H_5$ | —$CH_3$ | H | " | " | " |
| 12 | H | " | —$OCH_3$ | " | " | " |
| 13 | H | —$OCH_3$ | " | " | " | " |
| 14 | H | —$OCH_2CH_3$ | —$OCH_2CH_3$ | " | " | " |
| 15 | H | —$C_2H_5$ | H | " | " | " |
| 16 | H | —$CH_3$ | —$CH_3$ | " | " | " |
| 17 | H | " | H | —$CH_3$ | " | " |
| 18 | H | " | H | —$C_2H_5$ | —$CH_2$—$CHCH_3$ | " |
| 19 | H | " | H | " | —CH—CH—<br>    \|        \|<br>   $CH_3$  $CH_3$ | " |
| 20 | H | " | H | —$CH_2CH_2CH_3$ | —$CH_2CH_2$— | " |
| 21 | H | " | H | —$CH_2CH_2CH_2CH_3$ | " | " |
| 22 | —$CH_3$ | " | —$OCH_3$ | —$CH_2$—CH=$CH_2$ | " | —$CH_3$ |

TABLE-continued

| Ex. No. | $R_1$ | $R_2$ | $R_3$ | $R_4$ | $R_6$ | $R_5$ |
|---|---|---|---|---|---|---|
| 23 | " | " | H | $-CH_2CH_2CH_3$ | " | " |
| 24 | " | " | H | $-C_2H_5$ | " | $-CH_2CH_2OC_2H_5$ |
| 25 | " | " | H | $-CH_2-CH=CH_2$ | " | $-C_2H_5$ |
| 26 | H | $-OCH_3$ | H | " | " | $-CH_3$ |

APPLICATION EXAMPLE 7 parts of the dyestuff produced in accordance with Example 1 are ground to a fine powder for 48 hours in a ball mill with 4 parts of dinaphthylmethane disulphonic acid (sodium salt), 4 parts of sodium cetyl sulphate and 5 parts of anhydrous sodium sulphate.

1 Part of the dyeing preparation thus obtained is made into a paste with a little water and the suspension obtained is added, through a sieve, to a dye bath containing 3 parts of sodium lauryl sulphate in 4000 parts of water. The liquor ratio is 1:40. 100 Parts of scoured polyester fibre material are then added to the bath at 40°-50°, followed by 20 parts of a chlorinated benzene, emulsified in water. The bath is heated slowly to 100° and dyeing takes place for 1-2 hours at 95°-100°. The brilliant blue dyed material is washed, soaped, washed again and dried.

The level dyeing obtained shows good fastness to light, cross-dyeing, washing, water, sea water, perspiration, sublimation, gas fumes, thermofixation, pleating and permanent-pressing.

What is claimed is:

1. A compound of the formula

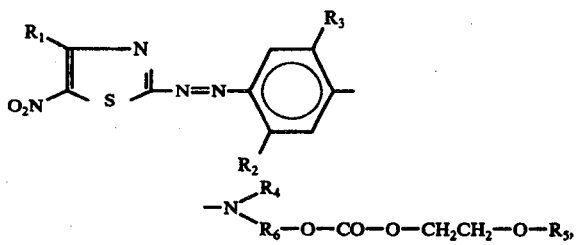

wherein $R_1$ is hydrogen, $C_{1-4}$alkyl, phenyl or substituted phenyl having 1 to 3 substituents each of which is independently chloro, bromo or cyano, with the proviso that the maximum number of cyano groups is one, $R_2$ is $C_{1-4}$alkyl or $C_{1-4}$alkoxy, $R_3$ is hydrogen, $C_{1-4}$alkyl or $C_{1-4}$alkoxy, $R_4$ is $C_{1-4}$alkyl or allyl, $R_5$ is $C_{1-4}$alkyl or $\beta$-($C_{1-4}$alkoxy) ethyl, and $R_6$ is $C_{2-4}$alkylene, with the proviso that the nitrogen atom and the oxygen atom to which $R_6$ is attached are not attached to the same carbon atom thereof.

2. A compound according to claim 1 wherein
$R_1$ is hydrogen or methyl,
$R_2$ is methyl or methoxy,
$R_3$ is hydrogen,
$R_4$ is ethyl, and
$R_5$ is methyl, ethyl, $\beta$-methoxyethyl or $\beta$-ethoxyethyl.

3. A compound according to claim 2 wherein $R_6$ is ethylene.

4. A compound according to claim 3 wherein
$R_2$ is methyl, and
$R_5$ is methyl or ethyl.

5. The compound according to claim 4 wherein
$R_1$ is hydrogen, and
$R_5$ is ethyl.

6. The compound according to claim 4 wherein
$R_1$ is methyl, and
$R_5$ is ethyl.

7. The compound according to claim 4 wherein
$R_1$ is hydrogen, and
$R_5$ is methyl.

8. The compound according to claim 1 wherein
$R_1$ is hydrogen,
$R_2$ is methyl,
$R_3$ is hydrogen,
$R_4$ is n-propyl,
$R_5$ is ethyl, and
$R_6$ is ethylene.

9. The compound according to claim 1 wherein
$R_1$ is methyl,
$R_2$ is methyl,
$R_3$ is hydrogen,
$R_4$ is n-propyl,
$R_5$ is methyl, and
$R_6$ is ethylene

* * * * *